United States Patent [19]

Eck

[11] Patent Number: 5,746,707

[45] Date of Patent: May 5, 1998

[54] CARPEL TUNNEL SYNDROME EXTERNAL BRACE

[76] Inventor: Donald R. Eck, 8965 E. Arthur Rd., Hesperia, Mich. 49421

[21] Appl. No.: 723,339

[22] Filed: Sep. 30, 1996

[51] Int. Cl.$^6$ ............................................. A61F 5/00
[52] U.S. Cl. ........................ 602/21; 602/22; 128/878; 128/879
[58] Field of Search ........................... 602/20–22, 64, 602/75, 6; 128/878–880

[56] References Cited

U.S. PATENT DOCUMENTS

| | | | |
|---|---|---|---|
| 1,220,476 | 3/1917 | Ujdur | 602/22 |
| 1,817,212 | 8/1931 | Siebrandt | 602/21 |
| 4,384,571 | 5/1983 | Nuzzo | 602/22 |
| 4,781,178 | 11/1988 | Gordon | 602/22 |
| 4,782,825 | 11/1988 | Lonardo | 128/77 |
| 4,850,341 | 7/1989 | Fabry et al. | 128/44 |
| 5,058,576 | 10/1991 | Grim | 602/21 |
| 5,121,743 | 6/1992 | Bishop | 602/22 |
| 5,356,371 | 10/1994 | Hubbard | 602/21 |
| 5,376,066 | 12/1994 | Phillips et al. | 602/64 X |
| 5,413,553 | 5/1995 | Downes | 602/21 |
| 5,417,645 | 5/1995 | Lemmen | 602/21 |
| 5,449,820 | 3/1995 | Albertsson | 128/879 X |
| 5,466,215 | 11/1995 | Lair et al. | 602/21 |
| 5,637,078 | 6/1997 | Varn | 128/878 X |

FOREIGN PATENT DOCUMENTS 406285108  10/1994  Japan ........................... 602/22

Primary Examiner—Richard J. Apley
Assistant Examiner—Denise Pothier
Attorney, Agent, or Firm—James A. Geppert

[57] ABSTRACT

A wrist and two digit restraining device for the treatment of carpal tunnel syndrome wherein the device comprises a palmar brace having a wrist support conformably receiving the wrist of a patient, a forward portion of the support supporting the heel and palm of the patient's hand and terminating at the base of the second, third and forth fingers of the hand, a thumb support extending at an angle from the forward portion of the support, a fifth finger support extending at an angle in the generally opposite direction from the thumb support, and attachment straps for the wrist support, the thumb support and the fifth finger support securing the device to the wrist, thumb and fifth finger over an extended period of time to create a fully abducted position of the thumb and fifth finger relative to the remainder of the hand with unrestricted motion of the second, third and fourth digits to relieve pressure on the median nerve in the wrist.

12 Claims, 2 Drawing Sheets

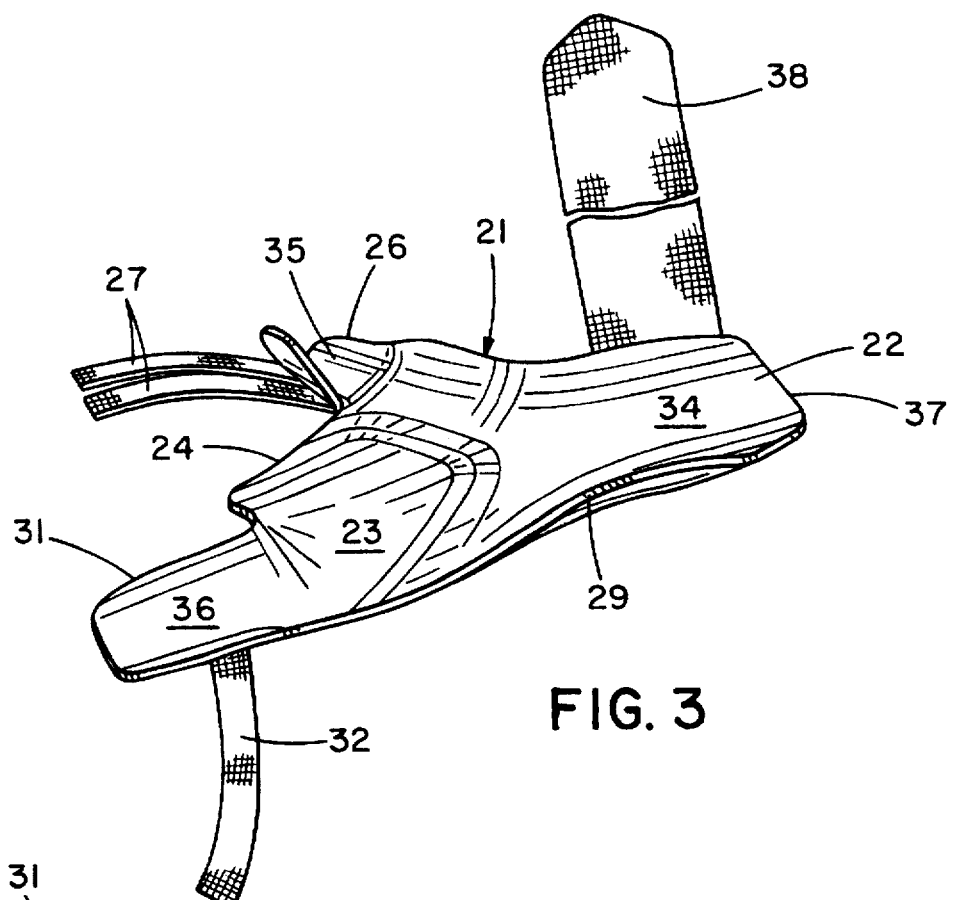
FIG. 3
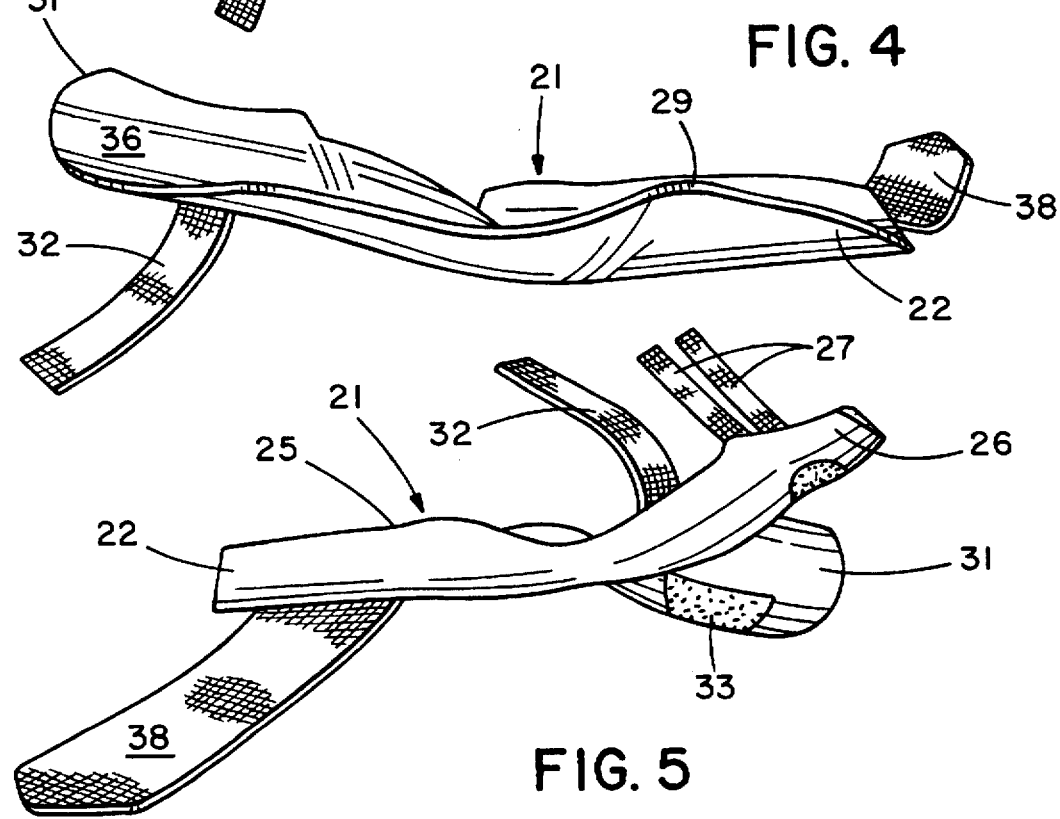
FIG. 4
FIG. 5

CARPEL TUNNEL SYNDROME EXTERNAL BRACE

TECHNICAL FIELD

The present invention relates to a medical device in the form of an external brace to be applied to the hand and wrist of a patient to relieve the symptoms of carpal tunnel syndrome.

BACKGROUND

Carpal tunnel syndrome is a pathological condition of the upper extremity and of the hand and finger caused by compression of the median nerve resulting in pain, numbness, paresthesia, and weakness of the affected part. In recent years, carpal tunnel syndrome has come into greater prominence because of hand intensive activities of workers in industry, its work related morbidity, and employee loss of work time.

In recent years, the more moderate and severe cases of carpal tunnel syndrome have succumbed to surgical intervention for relief of the symptoms; sometimes with good results, and sometimes with less than satisfactory results. The current pathophysiological concept of carpal tunnel syndrome is that an increase in the pressure of the chamber in the carpal tunnel ligament occupied by the median nerve and other structures results from swelling and inflammation within those chambers (tunnels) of the carpal tunnel ligament.

It is submitted that this theory was flawed due to findings at the time of surgical intervention of patients with carpal tunnel syndrome. It was found that most of the compression to the median nerve was distal to the carpal tunnel ligament and that the other structures contained within the ligament were not involved in a pathological process. After having performed many carpal tunnel operations and decompressing the affected median nerve, it was concluded that the carpal tunnel ligament and its contents were not the etiological agents of this disease or condition, but that the thenar and hypothenar muscles and their aponeurotic insertion were etiological factors to be considered.

As a result of this new information, the present invention was developed to relieve the pressure caused by the aponeurotic tightness over the median nerve.

SUMMARY OF THE INVENTION

The present invention relates to an external brace of a suitable design which will decrease the necessity for surgical intervention of the patient and relieve the pressure caused by the aponeurotic tightness over the median nerve caused by compression to the nerve distal to the carpal tunnel ligament. This brace has been tested on patients for approximately two years in experimental trials on confirmed cases of carpal tunnel syndrome. Confirmation of carpal tunnel syndrome was obtained by clinical examination and electro-diagnostic studies (EMG) of the affected extremity, and the results have been very promising. It is concluded that the basic etiological factor for carpal tunnel syndrome is overuse and subsequent hypertrophy of the thenar and hypothenar muscles of the hand. As a result of the hypertrophy of these muscles, a state of hypertonicity of the muscles occurs and causes an increase in the tension of the common aponeurotic insertion which is directly contiguous with the subjacent median nerve thus causing compression of the median nerve.

The brace itself performs three functions to accomplish the desired results:

1) A slight angular extension of the affected wrist.
2) A position of stretch for the thumb and fifth digit.
3) The allowance of free motion of the second, third and fourth digits of the involved extremity.

The brace includes a main support portion which extends under the wrist portion of the arm and the heel and the palm of the hand of the patient's extremity and outwardly extending support portions for the thumb and fifth digit of the hand so that the thumb and fifth digit are in a fully abducted position. A wrist strap adjacent the inner end of the brace clamps the brace onto the wrist and secondary straps are used to bind the thumb and fifth digit onto the supports for these digits. Over a period of time, use of this brace results in a marked reduction of night pain, numbness and paresthesia of the affected hand.

BRIEF DESCRIPTION OF THE DRAWINGS

FIG. 3 is a perspective view of the brace alone generally from the top of the brace.

FIG. 4 is a perspective view of the brace of FIG. 3 generally from one side of the brace.

FIG. 5 is a perspective view of the brace of FIG. 3 rotated 180 degrees and showing the opposite side of the brace from FIG. 4.

DISCLOSURE OF THE PREFERRED EMBODIMENT

Figure 1:
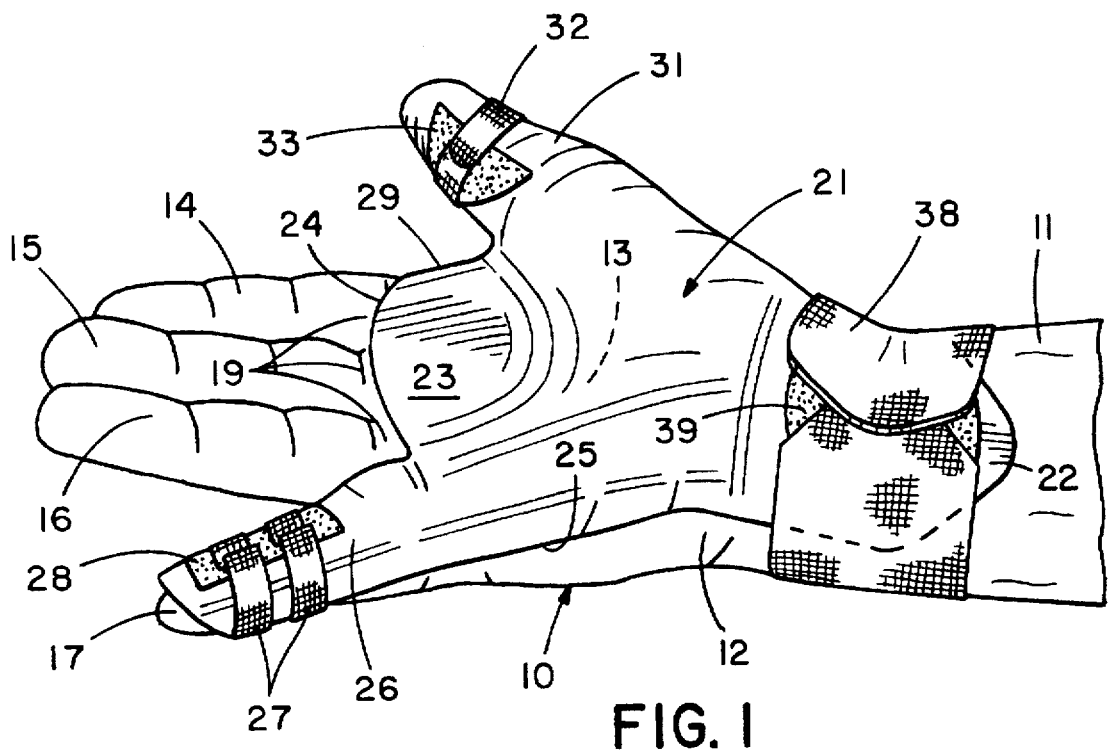
FIG. 1 is a perspective view of the right hand of a patient palm-up with the external brace applied thereto.

Referring more particularly to the disclosure in the drawings wherein is shown an illustrative embodiment of the present invention, FIG. 1 discloses the right hand 10 of a patient suffering from carpal tunnel syndrome which has the external brace 21 of the present invention applied thereto. It has been discovered that, although the present theory is that carpal tunnel syndrome is a result in an increase in the pressure of the chamber in the carpal tunnel ligament occupied by the median nerve and other structures due to swelling within those chambers or tunnels of the carpal tunnel ligament, present surgical experience appears to show that most of the compression to the median nerve was distal to the carpal tunnel ligament and that the other structure contained in the ligament were not involved in a pathological process. From that discovery, it came to light that the carpal tunnel ligament and its contents were not the etiological agents of this disease but that the thenar and hypothenar muscles and their aponeurotic insertion were etiological factors to be considered. Thus the brace 21 was designed which would relieve the pressure caused by the aponeurotic tightness over the median nerve.

The brace of the present invention was designed to accomplish this and has been tested in clinical trials on confirmed cases of carpal tunnel syndrome. Confirmation of carpal tunnel syndrome was obtained by clinical examination and electro-diagnostic studies (EMG) of the affected extremity with very promising results. The concept of the brace is based on the following physiological principles. It is submitted that the basic etiological factor for carpal tunnel syndrome is overuse and subsequent hypertrophy of the thenar and hypothenar muscles of the hand. As a result of the hypertrophy of these muscles, a state of hypertonicity of the muscles occurs and causes an increase in the tension of the common aponeurotic insertion which is directly contiguous with the subjacent median nerve thus causing compression of the median nerve.

The brace 21 includes an elongated proximal portion 22 supporting the wrist 11 of the hand 10 and a forward portion 23 extending over the heel 12 and palm 13 of the hand to terminate at the edge 24 at the base 19 of the fingers 14, 15 and 16. Extending at an angle from the edge front 24 and side edge 25 is an extension 26 for the fifth or little finger 17; the extension having one or more straps 27 with appropriate hook and loop type material 28 sold under the trademark VELCRO that overlaps to engage and retain the finger 17 at an angle from the other three fingers 14, 15 and 16. Opposite the side edge 25 is a side edge 29 having a second extension 31 which is substantially at a right angle or 90 degrees to the axis of the first extension 26. Here again, the extension for the thumb 18 has a strap 32 with a hook and loop type closure 33 to encircle and retain the thumb at an extreme outward angle, that is fully abducted, relative to the remainder of the hand, including the fifth finger.

As can be seen in FIGS. 3, 4 and 5, the brace 21 is provided with a concave shape at 34 to closely conform and support the wrist and hand of the patient and both the extensions 26 and 31 have a concave shape at 35 and 36, respectively, to accommodate the curvature of the finger and thumb of the patient. Also, secured to the proximal portion adjacent the rear end 37 of the brace is secured a generally wider strap 38 with a hook and loop type closure 39 to encircle the wrist of the patient and retain the brace in position thereon.

Figure 2:
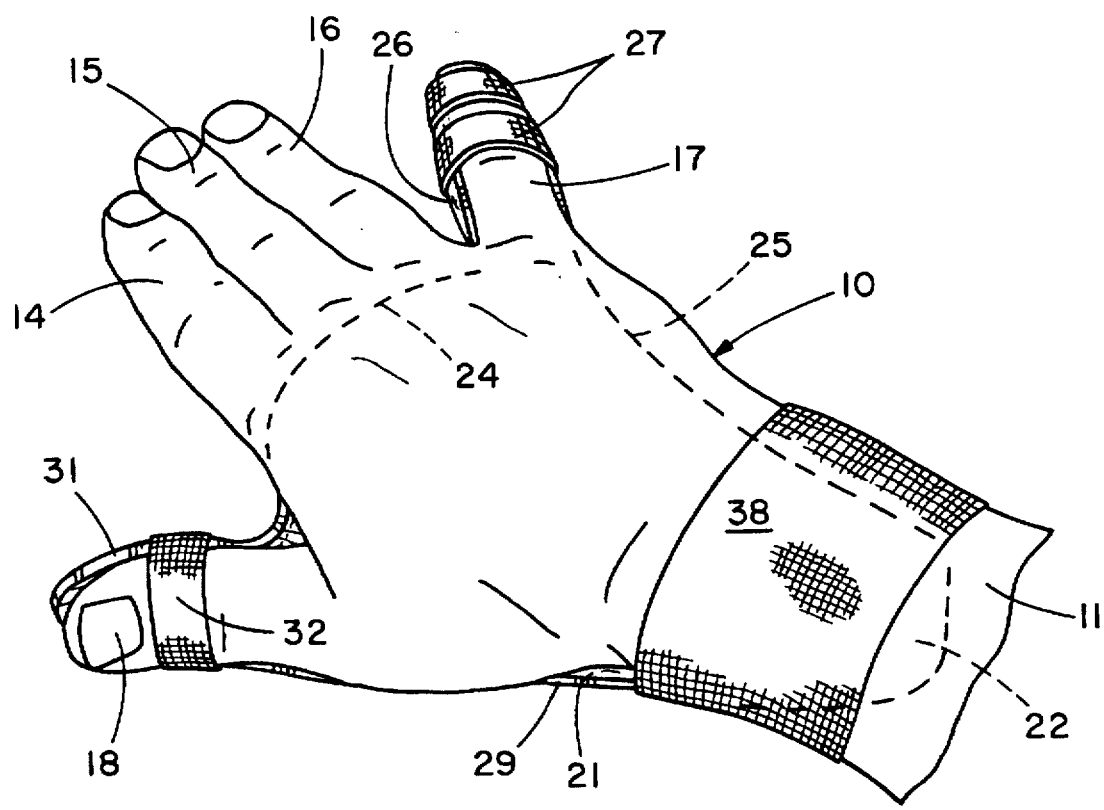
FIG. 2 is a perspective view of the patient's hand with the back up and showing the external brace applied under the hand.

The brace 21 itself performs three functions to accomplish its results in the treatment of carpal tunnel syndrome. First, the brace causes a slight angular extension as seen in FIG. 4 of the affected wrist. Second, the brace provides a position of stretch for the thumb 18 and fifth digit 17 as seen in FIGS. 1 and 2 by the angles of the extensions 26 and 31 relative to the forward portion 23. And third, the brace allows for freedom of motion of the 2nd, 3rd and 4th digits 14, 15 and 16 of the involved extremity. By stretching the thumb and fifth digit in a fully abducted position, the thenar and hypothenar muscles and their common aponeurotic insertion are caused to undergo fatigue and this relaxation decreases the median nerve compression when the brace 21 is worn for a sufficient period of time. Thus, the hypertonicity of the hypertrophied muscle decreases and, in turn, creates less compression of the median nerve. In the physician's hands, the patient wears the brace 21 as long as he or she can tolerate it, and then the brace is removed for a short period of time and the brace is reapplied. In most cases, two weeks of use of the brace in this fashion results in a marked reduction of night pain, numbness and paresthesia of the affected hand.

The brace is formed of an appropriate substantially rigid material, such as a suitable metal or rigid plastic material which is molded or otherwise formed into the desired shape of the brace conforming to the general outline of the patient's hand and wrist. Also, the brace may be appropriately lined with a relatively soft material to prevent abrasion or irritation to the skin of the patient and/or appropriately padded for comfort when the brace is applied onto the wrist and hand of the patient.

I claim:

1. In combination, a wrist and hand brace for application to the wrist and hand of a patient for the amelioration of the symptoms of carpal tunnel syndrome, the hand being connected to the wrist and including a heel, a palm, and four fingers and a thumb connected to the palm, the brace comprising a rigid base strip of a suitable moldable material having a generally concave shape conformably receiving the wrist of a patient, a forward portion of said strip covering the heel and palm of the hand and terminating adjacent the base of the fingers thereof, an integral thumb support extending at an angle from one side edge of the forward portion, an integral fifth finger support extending at an angle from a side edge of the forward portion opposite to the thumb support, and means joined to said strip and thumb and fifth finger supports for attaching said brace to the wrist, thumb and fifth finger of the patient to provide the thumb and fifth finger in generally fully abducted positions from the hand.

2. In combination, a wrist and hand brace for application to the wrist and hand of a patient for the amelioration of the symptoms of carpal tunnel syndrome, the hand being connected to the wrist and including a heel, a palm, and four fingers and a thumb, the brace comprising a rigid base strip having a generally concave shape conformably receiving the wrist of a patient, a forward portion of said strip covering the heel and palm of the hand and terminating adjacent the base of the fingers thereof, a thumb support extending at an angle from one side edge of the forward portion, a fifth finger support extending at an angle from of said forward portion, said thumb and fifth finger supports extending at approximately right angles to each other, and means joined to said strip and thumb and fifth finger supports for attaching said strip and supports to the wrist, thumb and fifth finger, respectively, of the patient.

3. The combination as set forth in claim 2, wherein said forward portion of said brace conformably receive the heel and palm portions of the hand of the patient.

4. The combination as set forth in claim 2, in which said attachment means comprises a strap secured to said wrist portion of said brace, a second strap secured to the thumb support, and a third strap secured to the fifth finger support of the brace.

5. The combination as set forth in claim 4, wherein each strap has free ends having hook and loop type material attachment means for securing the brace to the wrist, thumb and fifth finger of the patient.

6. The combination as set forth in claim 2, in which said thumb and fifth finger supports position the thumb and fifth finger of the patient to provide a slight angular extension of the affected wrist of the patient, and a position of stretch for the thumb and fifth finger.

7. The combination as set forth in claim 6, in which said forward portion of the brace terminates adjacent to the base of the second, third and fourth fingers to allow for freedom of motion of the digits of the involved extremity.

8. The combination as set forth in claim 6, wherein the brace provides for a substantially fully abducted position of the first and fifth digits causing the thenar and hypothenar muscles and their common aponeurotic insertion to undergo fatigue with the resultant relaxation decreasing the median nerve compression.

9. The combination as set forth in claim 2, in which said brace is formed of a suitable moldable material.

10. A method of alleviating a patient's carpel tunnel symptoms by treatment of a patient with carpal tunnel syndrome, including the steps of conformably receiving the wrist of the patient with a rigid base strip, supporting the heel and palm of the hand with a forward portion of the rigid base strip, supporting the thumb and fifth finger of the hand with a thumb support at a substantially right angle to a fifth finger support, and securing the rigid base to the wrist, the thumb support to the thumb and fifth finger support to the fifth finger of the patient.

11. The method as set forth in claim 10, in which the thumb and fifth finger are positioned in a fully abducted position relative to wrist and hand of the patient.

12. The method as set forth in claim 10, in which said wrist portion is concave to conformably receive the wrist of said support.

* * * * *

UNITED STATES PATENT AND TRADEMARK OFFICE
CERTIFICATE OF CORRECTION

PATENT NO. : 5,746,707
DATED : May 5, 1998
INVENTOR(S) : Donald R. Eck

It is certified that error appears in the above-identified patent and that said Letters Patent is hereby corrected as shown below:

Column 4, line 23, after "from", insert -- an opposite side edge --.

Signed and Sealed this

Twenty-sixth Day of October, 1999

Attest:

Q. TODD DICKINSON

Attesting Officer

Acting Commissioner of Patents and Trademarks